(12) United States Patent
Barrett

(10) Patent No.: US 9,532,813 B2
(45) Date of Patent: Jan. 3, 2017

(54) ANTERIOR LUMBAR INTERBODY GRAFT INSERTER

(71) Applicant: Pat Barrett, Jackson, MS (US)

(72) Inventor: Pat Barrett, Jackson, MS (US)

(73) Assignee: SPINAL U.S.A., Pearl, MS (US)

( * ) Notice: Subject to any disclaimer, the term of this patent is extended or adjusted under 35 U.S.C. 154(b) by 0 days.

(21) Appl. No.: 13/948,427

(22) Filed: Jul. 23, 2013

(65) Prior Publication Data

US 2014/0128929 A1 May 8, 2014

Related U.S. Application Data

(63) Continuation of application No. 13/433,667, filed on Mar. 29, 2012, now Pat. No. 8,518,046, which is a continuation of application No. 12/327,182, filed on Dec. 3, 2008, now Pat. No. 8,167,885.

(60) Provisional application No. 60/992,443, filed on Dec. 5, 2007.

(51) Int. Cl.
*A61B 17/70* (2006.01)
*A61F 2/46* (2006.01)

(52) U.S. Cl.
CPC ......... *A61B 17/7074* (2013.01); *A61F 2/4611* (2013.01); *A61F 2002/4622* (2013.01)

(58) Field of Classification Search
CPC ... A61B 17/7074; A61B 17/88; A61B 17/885; A61B 17/8872
USPC ................ 606/86 A, 86 B, 96, 99, 104, 190, 606/205–208
See application file for complete search history.

(56) References Cited

U.S. PATENT DOCUMENTS

| | | | |
|---|---|---|---|
| 1,219,726 A * | 3/1917 | Gray ...................... | A47J 43/283 294/3 |
| 5,284,487 A * | 2/1994 | Hartmeister ....... | A61B 17/2804 606/205 |
| 7,651,500 B2 * | 1/2010 | Supper ................. | A61B 17/025 606/90 |
| 8,167,885 B2 | 5/2012 | Barrett | |
| 8,518,046 B2 | 8/2013 | Barrett | |
| 2009/0210017 A1 | 8/2009 | Barrett | |

* cited by examiner

*Primary Examiner* — Ellen C Hammond
*Assistant Examiner* — Christina Negrellirodrigue
(74) *Attorney, Agent, or Firm* — Cermak Nakajima & McGowan LLP; Adam J. Cermak

(57) ABSTRACT

An anterior lumbar interbody graft (ALIG) inserter includes prongs at the tip of the inserter which can optionally grasp, and thus insert, anterior and anterior-lateral grafts.

4 Claims, 2 Drawing Sheets

ANTERIOR LUMBAR INTERBODY GRAFT INSERTER

This application is a Continuation of, and claims priority under 35 U.S.C. §120 to, U.S. application Ser. No. 13/433,667, filed 29 Mar. 2012, now U.S. Pat. No. 8,518,046, and therethrough to U.S. application Ser. No. 12/327,182, filed 3 Dec. 2008, now U.S. Pat. No. 8,167,885, which claims priority under 35 U.S.C. §119 to U.S. provisional Application No. 60/992,443, filed 5 Dec. 2007, the entireties of all of which are incorporated by reference herein.

BACKGROUND

Field of Endeavor

The present invention relates to devices and systems useful as interbody graft inserters.

Brief Description of the Related Art

Anterior lumbar interbody graft (ALIG) inserters on the market today can only be used for insertion of a single type of interbody graft, that is, they are only a one directional inserter. For example, one inserter is configured for insertion of an interbody graft into the L5-S1 locations, while another inserter is differently configured for the L3-L4, and L4-L5 applications.

There remains a need in the art for a single device which can be used for multiple applications, saving the surgeon time in surgery and reducing the risk of losing the ALIG inserters and reducing the confusion among the ALIG inserters by only having one ALIG inserter for multiple applications.

SUMMARY

One of numerous aspects of the present invention includes a tool useful for manipulating an anterior interbody graft, the tool comprising a handle section including a pair of handles movable toward and away from each other, a head section including a pair of jaws movable toward and away from each other, and an intermediate section joining the handle section to the head section, the intermediate section including a symmetrical four-bar linkage having four pivots, the four-bar linkage connecting together the pair of handles and the pair of jaws so that movement of the handles causes movement of the jaws, wherein each jaw includes a prong with a first thickness and a portion with a second thickness, the first thickness being smaller than the second thickness, wherein each jaw includes a shoulder where first and second thicknesses meet.

Still other aspects, features, and attendant advantages of the present invention will become apparent to those skilled in the art from a reading of the following detailed description of embodiments constructed in accordance therewith, taken in conjunction with the accompanying drawings.

BRIEF DESCRIPTION OF THE DRAWINGS

The invention of the present application will now be described in more detail with reference to exemplary embodiments of the apparatus and method, given only by way of example, and with reference to the accompanying drawings, in which.

DETAILED DESCRIPTION OF EXEMPLARY EMBODIMENTS

Figure 1:
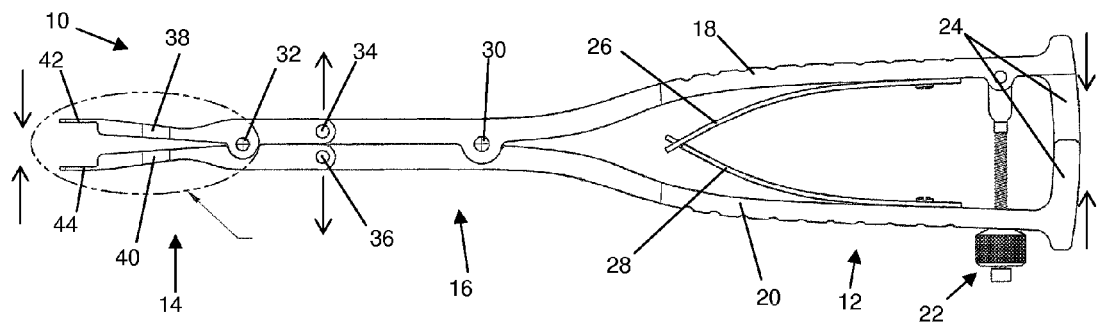
FIG. 1 illustrates a top plan view of an exemplary embodiment of a graft inserter embodying principles of the present invention.

Referring to the drawing figures, like reference numerals designate identical or corresponding elements throughout the several figures.

In general terms, the drawing figures illustrate an exemplary anterior lumbar interbody graft (ALIG) inserter embodying principles of the present invention. The ALIG inserter generally is a mechanism that holds an ALIG while being placed inside an intervertebral body. The inserter can be made out of any suitable material, including but not limited to (surgical) stainless steel, titanium, and any other material commonly used for surgical clamps, hemostats, and the like. As can be readily appreciated from the drawing figures, an inserter of the present invention can hold an ALIG in two ways: anterior, and anterior-lateral. Thus, an inserter in accordance with the present invention can eliminate the need for having two different inserters for anterior and anterior-lateral grafts. The prong(s) that hold onto the graft have a unique curvature that allows the inserter to rotate in either direction to hold onto either of the anterior and anterior-lateral grafts.

Turning now to the drawing figures, FIG. 1 illustrates a top plan view of an exemplary graft inserter tool 10 embodying principles of the present invention. The tool 10 includes a handle section 12, a head section 14, and an intermediate section 16 which connects together the handle and head sections and transmits force between the two sections.

The handle section 12 includes first and second handles 18, 20, as illustrated, in the manner of pliers, hemostats, and the like. An adjustment mechanism 22, in this exemplary embodiment including a threaded shaft connected to the handle 18 which extends through a hole in the handle 20, and a set nut, can be provided to limit the relative range of movement of the handles. A pair of guides 24 is provided on the handles, here at the proximal-most portion of the handles, to assist in keeping the handles aligned properly and to limit their range of motion towards each other. The handle section 12 also optionally includes a spring-loading mechanism, here exemplified by a pair of leaf springs 26, 28, attached to the inner surfaces of the handles 18, 20, which urges the handles back to an open orientation of the head section 14.

The intermediate section 16 transmits force and motion generated with the handle section 12 to the head section 14 of the tool 10. The intermediate section 16 includes one or more pivot points in order to gain mechanical advantage in the transmission of force. While the exemplary embodiment illustrated in the drawing figures includes three pivots, the present invention is not limited to this number, and can include fewer or more pivots as will be readily apparent to those of ordinary skill in the art.

The intermediate section 16 includes a first pivot 30 that joins together the two handles 18, 20 of the handle section 12, a second pivot 32 distal of the first pivot, and a pair of intermediate pivots 34, 36. The pivots 30-36 together form a four-bar linkage which transmits force and motion from the handle section 12 to the head section 14, in a known manner. More specifically, with reference to the three sets of arrows in FIG. 1 which depict directions of motion, motion of the handles 18, 20 toward each other cause the pivot points 34, 36 to move away from each other, which in turn causes the jaws 38, 40 of the head section 14 to move towards each other.

The head section 14 includes gripping jaws 38, 40, connected to the pivot 32 and the pivot points 34, 36. The gripping jaws 38, 40 are advantageously, yet not necessarily, mirror images of each other, and include features which permit the head section 14 to grasp and hold both anterior and anterior-lateral grafts. In particular, the jaws 38, 40 each include a prong 42, 44, respectively, which is configured to more easily grasp and hold both types of grafts.

Figure 2:
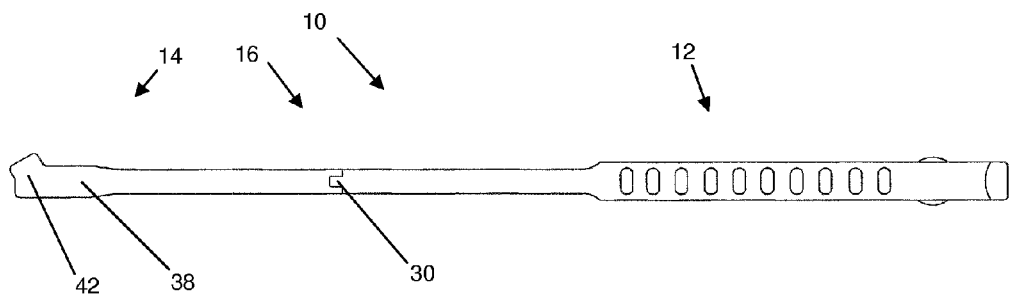
FIG. 2 illustrates a rear elevational view of the inserter of FIG. 1.
Figure 3:
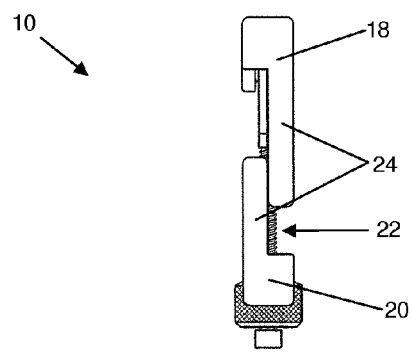
FIG. 3 illustrates a right side elevational view of the inserter of FIG. 1.

FIG. 2 illustrates a side elevational view of the inserter tool 10 of FIG. 1, and illustrates the handle section 12, head section 14, and intermediate section 16, pivot 30, jaw 38, and prong 42 thereof. As can be appreciated from FIG. 2, the jaw 38 advantageously includes a particular shape and other features which can assist in grasping and holding grafts. FIG. 3 illustrates a right elevational view of the inserter of FIG. 1, showing features of the handles 18, 20, the guides 24, and the adjustment mechanism 22.

Figure 4:
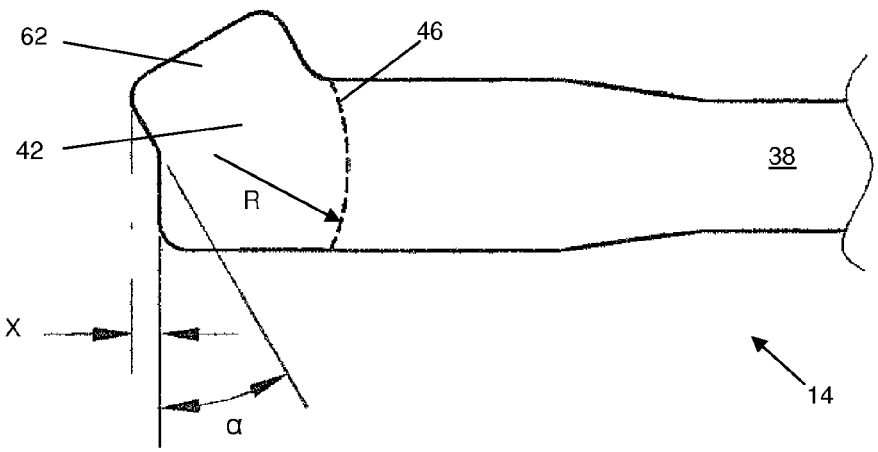
FIG. 4 illustrates an enlarged, side elevational view of the tip of the inserter of FIG. 1.

FIG. 4 illustrates an enlarged, front side elevational view of the head section 14 of the inserter tool 10 of FIG. 1. The jaws 38, 40 (only jaw 38 is described herein) can optionally include a stepped profile, moving from right to left in the drawing figure, leading to the prong 42 of the jaw. The prong 42 itself includes a tab 62 that extends away from the prong at a direction a (alpha) from a line perpendicular to the longitudinal axis of the jaw 38; in the embodiment illustrated in the drawing figures, the tab extends toward the bottom of the tool 10 (as FIG. 1 is a top plan view and FIGS. 2 and 4 are front elevational views), however the tab can alternatively extend toward the top of the tool. The angle α is between about 20 and 40 degrees, preferably between 27 and 33 degrees, more preferably about 30 degrees. Advantageously, the tab 62 also extends a longitudinal distance X from the rest of the prong 42, which is preferably between about 1 and 2 mm, more preferably about 1.6 mm.

Figure 5:
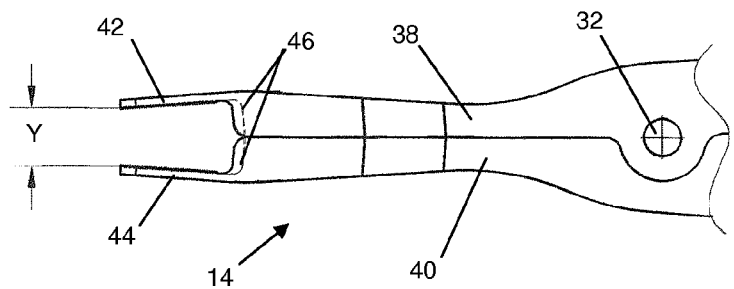
FIG. 5 illustrates an enlarged, top plan view of the tip portion indicated in FIG. 1, in a closed configuration.
Figure 6:
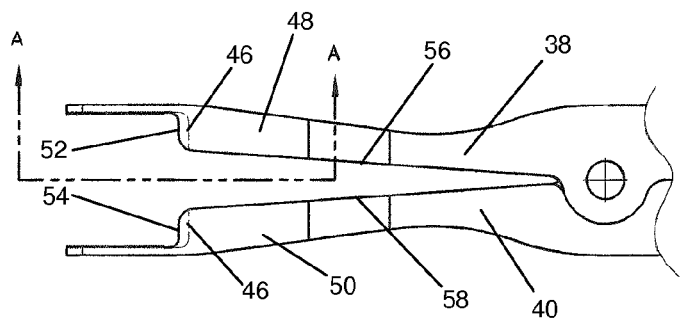
FIG. 6 illustrates an enlarged, top plan view of the tip portion indicated in FIG. 1, in an open configuration.
Figure 7:
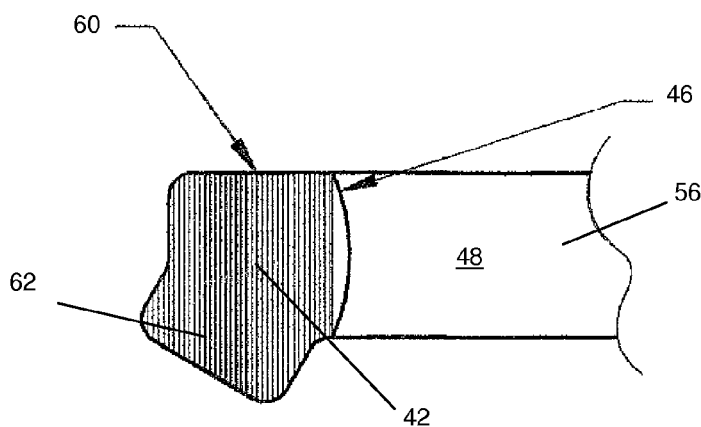
FIG. 7 illustrates the side elevational view taken at lines A-A in FIG. 6.

The jaws 38, 40 also advantageously include a portion of reduced cross-sectional width, which is more easily seen in the top plan views of FIGS. 5 and 6, while the profile of an end face portion of that reduced section is more easily understood from FIGS. 4 and 7. The jaws 38, 40 include endfaces 52, 54, each defined by a shoulder 46 which is advantageously not flat or linear. More specifically, the shoulder 46 is formed as a curved shoulder, and advantageously is formed at a radius R from a point distal of the shoulder, as illustrated in FIG. 4. Of course, the center of the curve that the shoulder 46 assumes does not have to be where it is illustrated in the drawing figure, as the radius R is preferably about 5 mm to about 20 mm, more preferably about 10.5 mm to about 14.5 mm, and more preferably about 12.5 mm. Furthermore, the shoulder 46 can be a shape other than circular, such as a portion of an ellipse, polygon, or another irregular shape.

With reference to FIGS. 5 and 6, the prongs 42, 44 of the jaws 38, 40 can be seen on the left end of the drawing, including the reduced cross-sectional portions described elsewhere herein. Because the shoulder 46 is, according to some embodiments, formed at a radius R, the views of FIGS. 5 and 6 necessarily show the shoulder 46 in phantom line and set back from the location where the shoulder meets the other end faces of the jaws. Furthermore, according to yet additional embodiments, the prongs 42, 44 are spaced apart from each other a distance Y when in the fully closed orientation of the head section 14, which is illustrated in FIG. 5. While the distance Y can be selected to match the grafts that are to be grasped by the tool 10, preferably Y is about 6 mm at the tips of the prongs. Additionally, and further optionally, the prongs 42, 44 are oriented at an angle towards each other and towards the centerline of the head section 14. This slight angling in of the prongs 42, 44, can be advantageous when, in the fully open orientation illustrated in FIG. 6, the prongs are parallel to each other so that they fit around a graft. More advantageously, the adjustment mechanism 22 is configured so that it permits adjustment of the maximum distance between the handles 18, 20 such that the prongs are parallel to each other, but also so that the prongs can be more or less spread apart, depending on the needs of the surgeon.

Also illustrated in FIGS. 5 and 6 are the unreduced, thicker portions 48, 50 of the jaws 38, 40, respectively, and the inner surfaces 56, 58 of the jaws 38, 40, which inner surfaces abut one another when the jaws are in a fully closed orientation.

FIG. 7 illustrates a side elevational view taken at lines A-A in FIG. 6, and thus illustrates the shoulder 46, the thicker portion 48 of the jaw 38, the inner surface 56 of that jaw, the prong 42, and the tab 62 extending from the prong. Advantageously, yet optionally, the inner surface of the prong 42 includes a roughened surface, such as with serrations 60, knurling, or the like, to assist the tool 10 in holding onto a graft when positioned between the prongs.

Exemplary methods, embodying principles of the present invention, will now be described with reference to the drawing figures. A medical practitioner, e.g., a surgeon, takes the tool 10 in her hand inserts a portion of an anterior lumbar interbody graft, in either an anterior or an anterior-lateral orientation, between the prongs. She then squeezes the handles 18, 20 together, against the force provided by the springs, which moves the jaws 38, 40 from their open orientation (FIG. 6) to their closed orientation (FIG. 5). The practitioner then maintains pressure on the handles, thus holding the graft between the prongs, and uses the tool 10 to insert the graft into the patient, depending on whether the graft is for anterior or anterior-lateral placement, either anteriorly or anterior-laterally. Once the graft is inserted into the intervertebral disc space the inserter is removed from the graft.

While the invention has been described in detail with reference to exemplary embodiments thereof, it will be apparent to one skilled in the art that various changes can be made, and equivalents employed, without departing from the scope of the invention. The foregoing description of the preferred embodiments of the invention has been presented for purposes of illustration and description. It is not intended to be exhaustive or to limit the invention to the precise form disclosed, and modifications and variations are possible in light of the above teachings or may be acquired from practice of the invention. The embodiments were chosen and described in order to explain the principles of the invention and its practical application to enable one skilled in the art to utilize the invention in various embodiments as are suited to the particular use contemplated. It is intended that the scope of the invention be defined by the claims appended hereto, and their equivalents. The entirety of each of the aforementioned documents is incorporated by reference herein.

What is claimed is:

1. A tool useful for manipulating an anterior interbody graft, the tool comprising:
   a proximal handle section including a pair of handles movable toward and away from each other;
   a distal head section including a pair of jaws movable toward and away from each other; and
   an intermediate section joining the handle section to the head section, the intermediate section including a symmetrical four-bar linkage having four pivots, the four-bar linkage connecting together the pair of handles and the pair of jaws so that movement of the handles causes movement of the jaws;
   wherein each jaw includes a prong with a distal end, a first thickness adjacent to said distal end, and a portion with a second thickness, the first thickness being smaller than the second thickness;
   wherein each jaw includes a distally facing shoulder where said first and second thicknesses meet.

2. A tool according to claim 1, wherein the shoulder has a radius.

3. A tool according to claim 1, wherein the head section, the intermediate section, and the handle section are mutually configured and arranged so that movement of the handles toward each other causes movement of the jaws toward each other.

4. A tool according to claim 1, wherein the head section is configured and arranged so that the jaws have an open orientation and a closed orientation, the prongs spaced apart and angling toward each other in the closed orientation.

* * * * *